(12) United States Patent
Shiba et al.

(10) Patent No.: US 10,130,250 B2
(45) Date of Patent: Nov. 20, 2018

(54) OCT DATA PROCESSING APPARATUS AND OCT DATA PROCESSING PROGRAM

(71) Applicant: NIDEK CO., LTD., Gamagori, Aichi (JP)

(72) Inventors: Ryosuke Shiba, Aichi (JP); Yasuhiro Furuuchi, Aichi (JP); Tetsuya Kano, Aichi (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 0 days.

(21) Appl. No.: 15/340,346

(22) Filed: Nov. 1, 2016

(65) Prior Publication Data

US 2017/0119244 A1 May 4, 2017

(30) Foreign Application Priority Data

Nov. 2, 2015 (JP) .................................. 2015-216182
Nov. 2, 2015 (JP) .................................. 2015-216183

(51) Int. Cl.
*G06K 9/00* (2006.01)
*A61B 3/00* (2006.01)
(Continued)

(52) U.S. Cl.
CPC .......... *A61B 3/0025* (2013.01); *A61B 3/0041* (2013.01); *A61B 3/102* (2013.01); *A61B 3/1233* (2013.01); *G06K 9/0061* (2013.01); *G06K 9/00604* (2013.01); *G06K 9/4661* (2013.01); *G06K 9/6202* (2013.01);
(Continued)

(58) Field of Classification Search
CPC ..... A61B 3/0025; A61B 3/0041; A61B 3/102; A61B 3/12; A61B 3/1233; A61B 3/1241; A61B 5/14555; A61B 8/10; A61B 2576/00; A61B 2576/02; G06K 9/00604; G06K 9/0061; G06K 9/4661; G06K 9/6202; G06K 9/00496; G06K 9/00597; G06K 2209/00932; G06K 2209/00939; G06T 7/0012; G06T 7/00; G06T 7/20; G06T 7/254; G06T 7/0016; G06T 2207/30041; G06T 2207/10101; G06T 2210/41; G06F 19/30–19/325; G06F 19/34; G06F 19/36; Y10S 348/901
See application file for complete search history.

(56) References Cited

U.S. PATENT DOCUMENTS 8,879,813 B1* 11/2014 Solanki ................. G06T 7/0014
382/128
2010/0208204 A1* 8/2010 Imamura ................. A61B 3/102
351/206

(Continued)

FOREIGN PATENT DOCUMENTS

JP         2014-139225 A      7/2014

*Primary Examiner* — Jose L Couso
(74) *Attorney, Agent, or Firm* — Sughrue Mion, PLLC

(57) ABSTRACT

An OCT data processing device for processing OCT data of a subject eye includes: a processor; and memory storing computer readable program, when executed by the processor, causing the OCT data processing device to execute: acquiring OCT data from an OCT optical system; and analyzing the acquired OCT data to acquire arteriovenous information on the blood vessel based on image information on a blood vessel scan area including a blood vessel of the subject eye.

16 Claims, 10 Drawing Sheets

(51) Int. Cl.
*A61B 3/10* (2006.01)
*A61B 3/12* (2006.01)
*G06T 7/00* (2017.01)
*G06K 9/46* (2006.01)
*G06K 9/62* (2006.01)

(52) U.S. Cl.
CPC ........ *G06T 7/0012* (2013.01); *G06K 2209/05* (2013.01); *G06T 2207/10101* (2013.01); *G06T 2207/30041* (2013.01); *G06T 2207/30101* (2013.01)

(56) References Cited

U.S. PATENT DOCUMENTS

| | | | |
|---|---|---|---|
| 2011/0102742 A1* | 5/2011 | Miyasa | A61B 3/102 351/206 |
| 2012/0218517 A1* | 8/2012 | Imamura | A61B 3/1241 351/206 |
| 2015/0313466 A1* | 11/2015 | Yoshida | A61B 5/0066 600/425 |
| 2015/0313467 A1* | 11/2015 | Sakai | A61B 3/102 351/208 |
| 2015/0348287 A1* | 12/2015 | Yi | G06T 11/003 382/131 |
| 2016/0198951 A1* | 7/2016 | Fujino | A61B 3/1005 351/206 |
| 2016/0317016 A1* | 11/2016 | Oishi | A61B 3/102 |
| 2017/0100030 A1* | 4/2017 | Bedworth | A61B 3/0025 |
| 2017/0347880 A1* | 12/2017 | Akiba | A61B 3/12 |

\* cited by examiner

OCT DATA PROCESSING APPARATUS AND OCT DATA PROCESSING PROGRAM

CROSS REFERENCE TO RELATED APPLICATION

This application is based upon and claims the benefit of priorities of Japanese Patent Application No. 2015-216182 filed on Nov. 2, 2015 and Japanese Patent Application No. 2015-216183 filed on Nov. 2, 2015, the contents of which are incorporated herein by reference in its entirety.

The present invention relates to an OCT data processing device and an OCT data processing program for processing OCT data on subject eyes.

In the related art, a technology for calculating a ratio between the blood vessel diameter of an artery and the blood vessel diameter of a vein (hereinafter, referred to as an "arteriovenous ratio") with respect to a fundus of a subject eye by acquiring a front image of the fundus with a fundus camera and processing the front image. For example, a fundus image processing device of patent literature 1 detects blood vessels from a front image of a fundus, and determines thin blood vessels having high luminance and thick blood vessels having low luminance as arteries and veins, respectively.

PRIOR TECHNICAL LITERATURE

Patent Literature

[Patent literature 1] Japanese Patent Application Laid-Open No. 2014-193225

DISCLOSURE OF INVENTION

Problem to be Solved by the Invention

However, from some fundus front images acquired with fundus cameras like in the device of the related art, it is impossible to accurately determine arteries and veins.

The present invention was made in view of the problem of the related art, and a technical object of the present invention is to provide an OCT data processing device and an OCT data processing program for efficiently acquiring arteriovenous information on blood vessels of a fundus.

In order to achieve the above-described object, the present invention is characterized by the following configurations.

(1) An OCT data processing device for processing OCT data of a subject eye, comprising:

a calculating unit configured to analyze OCT data acquired by an OCT optical system, wherein the calculating unit acquires arteriovenous information on the blood vessel based on image information on a blood vessel scan area including a blood vessel of the subject eye.

(2) An OCT data processing program which is executable in an OCT data processing device configured to process OCT data of a subject eye, and is executed by a processor of the OCT data processing device, thereby making the OCT data processing device perform the following:

an acquiring step of analyzing OCT data acquired by an OCT optical system, and acquiring arteriovenous information on a blood vessel of the subject eye based on image information on a blood vessel scan area including the blood vessel.

MODE OF CARRYING OUT THE INVENTION

Figure 1:
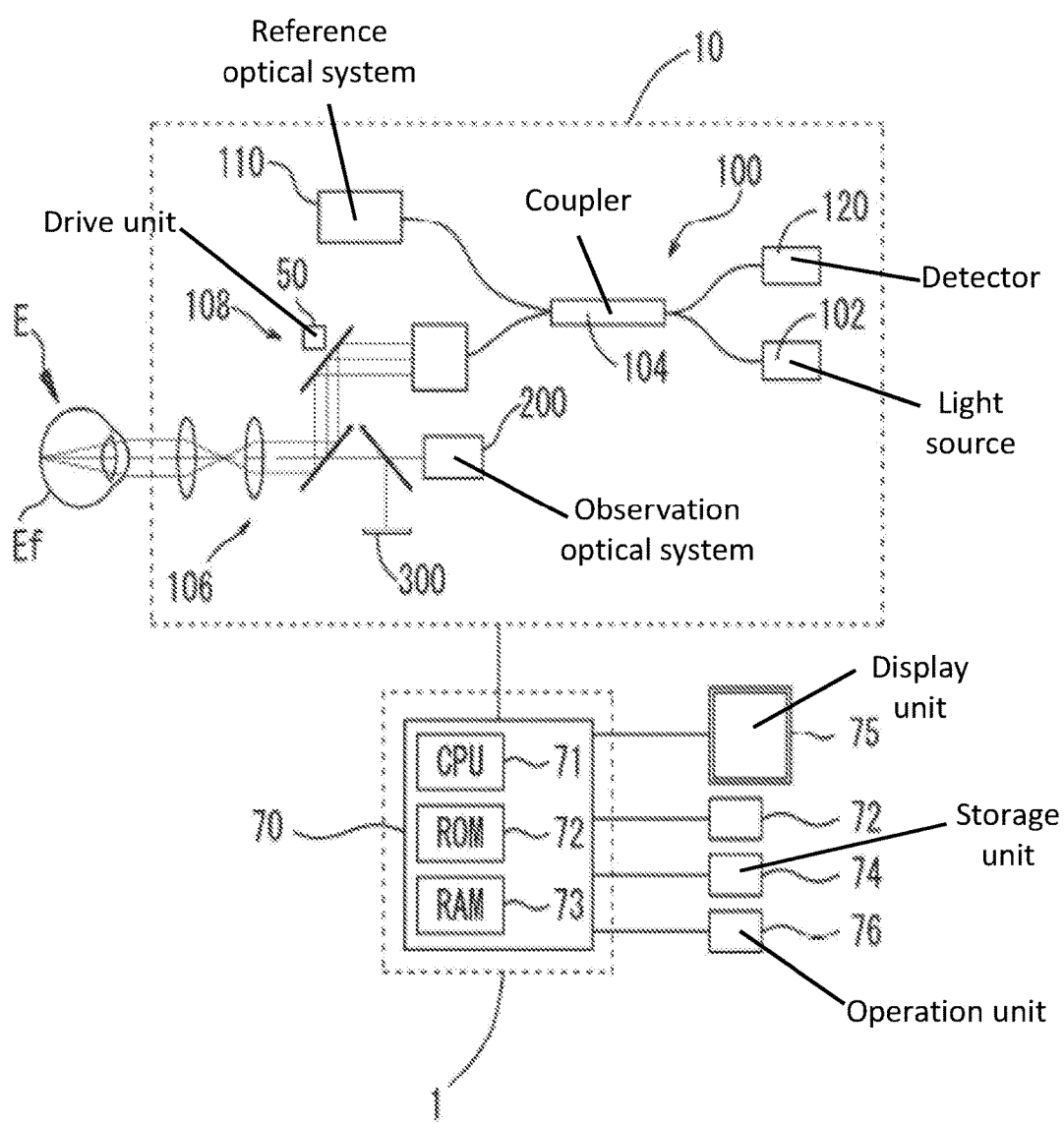
FIG. 1 is a schematic configuration diagram for explaining the configuration of an OCT data processing device according to an example.

Hereinafter, an OCT data processing device of a first embodiment will be described in brief. The OCT data processing device of the first embodiment (for example, an OCT data processing device 1) processes, for example, OCT data. Examples of OCT data include tomographic image data, three-dimensional tomographic image data, and en-face image data acquired by OCT devices (for example, an OCT device 10). Tomographic image data is, for example, B-scan image data which can be generated by arranging OCT data items of an A-scan direction (also referred to as a depth direction or an optical axis direction) in a B-scan direction (a transverse direction or a direction parallel to a fundus). Three-dimensional tomographic image data is, for example, three-dimensional image data which can be generated by arranging B-scan images in a C-scan direction. En-face image data is, for example, image data of at least a portion of three-dimensional OCT data which can be generated by arranging B-scan image data items in the C-scan direction, as seen from an optical axis direction. The term "en-face" may mean a plane parallel to a surface of a fundus, or a two-dimensional horizontal tomographic plane.

OCT data is distinguished from motion contrast data in that OCT data is fundus reflection data. Motion contrast data is, for example, data generated based on a plurality of OCT signals acquired from the same acquisition position at different times, and is information representing motion of an object.

The OCT data processing device 1 includes, for example, a calculating unit (for example, a CPU 71). The calculating unit analyzes, for example, OCT data acquired by an OCT device. The calculating unit may acquire arteriovenous information on a blood vessel area of OCT data, for example, by analyzing the OCT data. To acquire arteriovenous information, luminance information of OCT data may be used. In this case, the calculating unit acquires arteriovenous information on blood vessels of a subject eye, for example, based on image information on a blood vessel scan area including the blood vessels. In this way, it is possible to efficiently acquire arteriovenous information on subject eyes.

In a case where OCT data is acquired, a fundus is scanned in a transverse direction by an optical scanner of an OCT device, and OCT data corresponding to a scan area on the fundus scanned by the optical scanner is acquired. A blood vessel scan area may be, for example, an area which is a data area included in OCT data and corresponding to a scan area positioned on a fundus and including blood vessels. In this case, arteriovenous information on a blood vessel area included in a blood vessel scan area may be acquired by analyzing image information on a corresponding data area.

Arteriovenous information is, for example, arteriovenous information specifying whether each blood vessel is an artery or a vein. Arteriovenous information may be information related to either arteries or veins, or may be, for example, information related to only arteries or information related to only veins. The arteriovenous information may be blood vessel distribution information related to arteries and/or veins.

The calculating unit may detect blood vessel walls from a blood vessel scan area. In this case, the calculating unit may acquire arteriovenous information on blood vessels, for example, based on luminance information on the blood vessel walls. The calculating unit can more appropriately acquire arteriovenous information by using blood vessel wall information.

The calculating unit may detect the luminance value of the wall of a blood vessel and the luminance value of a hollow surrounded by the blood vessel wall, from a blood vessel scan area, and compare them. In this case, if the luminance value of the blood vessel wall is larger than the luminance value of the hollow, the calculating unit may acquire arteriovenous information representing that the blood vessel is an artery; whereas if the luminance value of the blood vessel wall is smaller than the luminance value of the hollow, the calculating unit may acquire arteriovenous information representing that the blood vessel is a vein.

The calculating unit may acquire arteriovenous information on a plurality of blood vessels by comparing OCT data image information items of a plurality of blood vessel scan areas of OCT data corresponding to the plurality of blood vessels. In this way, the calculating unit can acquire appropriate arteriovenous information from relative information on a plurality of blood vessels.

The calculating unit may compare luminance values of a plurality of blood vessel scan areas. In this case, the calculating unit may acquire arteriovenous information representing that blood vessels included in some blood vessel scan areas included in the plurality of blood vessel scan areas and having relatively large luminance values are arteries, and acquire arteriovenous information representing that blood vessels included in some blood vessel scan areas included in the plurality of blood vessel scan areas and having relatively small luminance values are veins.

The calculating unit may acquire arteriovenous information on a plurality of blood vessels by separating a fundus of OCT data into a plurality of layers and compares image information items on at least one layer of the plurality of layers corresponding to a plurality of blood vessel scan areas. In this case, the calculating unit can use image information on layers likely to be influenced by arteries and veins to acquire appropriate arteriovenous information.

The calculating unit may compare luminance values of a plurality of blood vessel scan areas of at least one layer of the plurality of layers. In this case, the calculating unit may acquire arteriovenous information representing that blood vessels included in some blood vessel scan areas included in the plurality of blood vessel scan areas and having relatively large luminance values are arteries, and acquire arteriovenous information representing that blood vessels included in some blood vessel scan areas included in the plurality of blood vessel scan areas and having relatively small luminance values are veins.

The calculating unit may control a display unit (for example, a display unit 75) such that the display unit displays arteriovenous information. For example, the calculating unit may control a display unit such that the display unit displays arteriovenous information on a front image of the fundus of a subject eye. The calculating unit may control a display unit such that the display unit displays arteriovenous information on a three-dimensional motion contrast image acquired by an OCT optical system.

The calculating unit may change arteriovenous information based on an operation signal output in response to an operation on an operation unit (for example, an operation unit 76). In this case, an examiner can reflect experiences of the examiner to arteriovenous information.

The calculating unit may execute an OCT data processing program stored in a storage unit (such as a ROM 72, a RAM 73, or a storage unit 74). The OCT data processing program may include, for example, an acquiring step of analyzing OCT data acquired by the OCT optical system and acquiring arteriovenous information on blood vessels of a subject eye based on image information on blood vessel scan areas including the blood vessels.

Hereinafter, an OCT data processing device of a second embodiment will be described in brief. The OCT data processing device of the second embodiment (for example, the OCT data processing device 1) processes, for example, OCT data of a subject eye acquired by an OCT device (for example, the OCT device 10). The OCT data processing device mainly includes, for example, a control unit (for example, the CPU 71) for controlling display of a display unit (for example, the display unit 75). The control unit displays, for example, an A-scan profile corresponding to a blood vessel scan area including blood vessels, together with OCT data, on the display unit. In this way, the examiner can check the relationship between OCT data and an A-scan profile at the positions of blood vessels in a subject eye.

The control unit may display, for example, a first mark representing the position of the center or blood vessel wall of a blood vessel in a blood vessel scan area in the A-scan direction, on OCT data. In this way, the control unit can easily present the positions of blood vessels on OCT data in the A-scan direction.

The control unit may display, for example, a second mark representing the position of the center or blood vessel wall of a blood vessel in a blood vessel scan area in the A-scan direction, on an A-scan profile. In this way, the control unit can easily present the positions of blood vessels on an A-scan profile in the A-scan direction.

The control unit may change the position of a first mark, for example, based on an operation signal output in response to an operation on an operation unit (for example, the operation unit 76). In this case, the examiner can input the position of a blood vessel on OCT data in the A-scan direction, based on experiences of the examiner.

The control unit may change the position of a first mark or a second mark, for example, based on an operation signal output in response to an operation on the operation unit. In this case, the examiner can input the position of a blood vessel on OCT data or an A-scan profile in the A-scan direction, based on experiences of the examiner.

The control unit may change the position of one of a first mark and a second mark while changing the other of the first mark and the second mark. In this case where the first mark and the second mark are movable in response to movement of each other, the examiner can check the positional relation correspondence between the first mark and the second mark.

A first mark or a second mark may be a mark representing at least one of the position of the outer wall of a blood vessel in the A-scan direction, the position of the inner wall of a blood vessel in the A-scan direction, and the position of the center of a blood vessel in the A-scan direction.

The control unit may display OCT data and an A-scan profile, for example, such that they overlap. In this case, it is easy to check the correspondence relationship between the OCT data and the A-scan profile.

The control unit may perform A-scan profile switching between a luminance profile and a gradient profile. In this case, the control unit can present, for example, a plurality of information items on an A-scan profile.

The control unit may execute an OCT data processing program stored in a storage unit (such as the ROM 72, the RAM 73, or the storage unit 74). The OCT data processing program may include, for example, a display step of displaying an A-scan profile corresponding to a blood vessel scan area including blood vessels of a subject eye, together with OCT data, on the display unit.

EXAMPLES

Hereinafter, an OCT data processing device of an example will be described based on the accompanying drawings. An OCT data processing device 1 (see FIG. 1) processes, for example, OCT data on a subject eye acquired by an optical coherence tomography device 10. The OCT data processing device includes, for example, a control unit 70. The control unit 70 includes, for example, a general central processing unit (CPU) 71, a ROM 72, a RAM 73, and so on. For example, in the ROM 72, an OCT data processing program for processing OCT data, various programs for controlling operations of the OCT device 10, initial values, and so on are stored. For example, the RAM 73 is for temporarily storing a variety of information.

As shown in FIG. 1, the control unit 70 is connected, for example, to a storage unit (for example, a non-volatile memory) 74, an operation unit 76, a display unit 75, and so on, such that communication is possible. The storage unit 74 is, for example, a non-transitory storage medium capable of retaining storage contents even if supply of power is interrupted. For example, the storage unit 74 may be a hard disk drive, a flash ROM, an attachable/detachable USB memory, or the like.

To the operation unit 76, various operation instructions of an examiner are input. The operation unit 76 outputs signals based on the input operation instructions to the CPU 71. As the operation unit 76, for example, at least one user interface of a mouse, a joy stick, a keyboard, a touch panel, and the like may be used.

The display unit 75 may be a display mounted on the main body of the device 1, or may be a display connected to the main body. For example, a display of a personal computer (hereinafter, referred to as a "PC") may be used. A plurality of displays can be used together. The display unit 75 may be a touch panel. In this case where the display unit is a touch panel, the display unit 75 may also be used as the operation unit 76. The display unit 75 displays, for example, OCT data and the like acquired by the OCT device 10.

The OCT data processing device 1 of the present example is connected, for example, to the OCT device 10. The connection method may be a wireless method, a wired method, or a combination of them. The OCT data processing device 1 may be configured integrally with the OCT device 10 inside a single case, or may be configured separately from the OCT device. The control unit 70 may acquire OCT data and the like from the connected OCT device 10. Obviously, the control unit 70 may not be connected to the OCT device 10. In this case, the control unit 70 may acquire OCT data obtained by performing imaging with the OCT device 10, through a storage medium.

<OCT Device>

Hereinafter, an outline of the OCT device 10 will be described based on FIG. 1. For example, the OCT device 10 acquires a tomographic image or the like of, for example, a fundus Ef of an eye E of an examinee. The OCT device 10 includes an interference optical system (OCT optical system) 100, a front observation optical system 200, and a fixation target projecting unit 300.

<OCT Optical System>

The OCT optical system 100 has the configuration of a so-called optical coherence tomography (OCT) device, and acquires tomographic images and the like of eyes E. The OCT optical system 100 splits light emitted from a measurement light source 102 into measurement light (sample light) and reference light by a coupler (a light splitter) 104. Further, the OCT optical system 100 guides the measurement light to a fundus Ef of an eye E by a measuring optical system 106, and guides the reference light to a reference optical system 110. Thereafter, interference light obtained by synthesizing the measurement light reflected by the fundus Ef and the reference light is guided to a detector (a light receiving device) 120.

The detector 120 detects the interference state of the measurement light and the reference light. In a case of Fourier domain OCT, the spectral intensity of the interference light is detected by the detector 120, and a depth profile (an A-scan signal) of a predetermined range is acquired by performing Fourier transform on spectral intensity data. Examples of OCT include spectral-domain OCT (SD-OCT), swept-source OCT (SS-OCT), and time-domain OCT (TD-OCT).

The scanning unit 108 scans the fundus of a subject eye with light emitted from the measurement light source. For example, the scanning unit 108 scans the fundus two-dimensionally (in X and Y directions (a transverse direction)) with the measurement light. The scanning unit 108 is disposed at a position substantially conjugate to a pupil. The scanning unit 108 may include, for example, a drive unit 50, and two Galvano mirrors 51 and 52. In this case, the reflection angles of the Galvano mirrors 51 and 52 can be adjusted by the drive unit 50.

In this configuration, the reflection (traveling) direction of a beam emitted from the light source 102 can be changed such that the fundus is scanned in an arbitrary direction with the beam. Therefore, a position on the fundus Ef to be imaged can be changed. As the scanning unit 108, a component for deflecting light may be used. For example, besides reflective mirrors (Galvano mirrors, polygon mirrors, and resonant scanners), other devices such as an acousto-optic device (an AOM) for changing the traveling (deflection) direction of light can be used.

The reference optical system 110 generates the reference light to be synthesized with the reflected light of the measurement light from the fundus Ef. The reference optical system 110 may be a Michelson type, or may be a Mach-Zehnder type. The reference optical system 110 is formed, for example, by a reflective optical system (for example, a reference mirror), such that light from the coupler 104 is reflected by the reflective optical system, thereby the light is guided to the coupler 104 again and then guided to the detector 120. As another example, the reference optical system 110 is formed by a transmissive optical system (for example, an optical fiber), such that light from the coupler 104 passes through the reference optical system, without being returning, thereby being guided to the detector 120.

The reference optical system 110 has a component for moving optical members positioned on a reference light path, thereby changing a difference in light path length between the measurement light and the reference light. For example, a reference mirror can be moved in an optical axis direction. The component for changing a difference in light path length may be disposed on a measurement light path of the measuring optical system 106.

<Front Observation Optical System>

The front observation optical system (a front image observation device) 200 is provided for acquiring a front image of a fundus Ef. The observation optical system 200 may be, for example, a so-called ophthalmic scanning laser ophthalmoscope (SLO) for two-dimensionally scanning a fundus with the measurement light (for example, infrared light) emitted from the light source, and receiving the reflected light from the fundus through a confocal aperture disposed at a position substantially conjugate to the fundus.

The configuration of the observation optical system 200 may be a so-called fundus camera type configuration. The OCT optical system 100 may also be used as the observation optical system 200. In other words, two-dimensional data to form a tomographic image may be used to acquire a tomographic image (for example, an image obtained by integrating data of a three-dimensional tomographic image in a depth direction, values obtained by integrating spectral data of positions corresponding to each pair of X and Y coordinates, luminance data of positions having X and Y coordinates at a certain depth, or an image of a surface layer of a retina).

<Fixation Target Projecting Unit>

The fixation target projecting unit 300 is for fixing the gaze direction of a subject eye E. For example, the fixation target projecting unit 300 has a fixation target to be present for an eye E. For example, the fixation target projecting unit 300 may have a visible light source for emitting visible light. The fixation target projecting unit 300 may lead the gaze direction of an eye E by moving the position of the fixation target.

<Control Operation>

With respect to the device having the above-described configuration, a control operation thereof will be described. The examiner instructs an examinee to fix an eye on the fixation target of the fixation target projecting unit 300, and then performs an alignment operation by the operation unit while watching an anterior eye part observation image acquired by an anterior eye part observation camera (not shown in the drawings) and displayed on the display unit 75, such that the axis of the measurement light passes through the center of the pupil of the subject eye.

Thereafter, the CPU 71 controls driving of the scanning unit 108 such that the scanning unit scan the fundus with the measurement light, and acquires a light reception signal corresponding to each scan area, from the detector 120, to acquire OCT data. For example, while CPU acquires the OCT data by the OCT optical system 100 and controls the observation optical system 200 to acquire a fundus front image. Further, as needed, the control unit 70 acquires OCT data and fundus front images by the OCT optical system 100 and the observation optical system 200, respectively.

<Image Analysis>

Subsequently, the CPU 71 performs analysis of OCT data stored in the storage unit 74. Hereinafter, an analyzing method of the present example will be described based on a flow chart of FIG. 2. First, in STEP S1, the CPU 71 performs blood vessel area detection on OCT data.

<Blood Vessel Area Detection (Step S1)>

Hereinafter, a blood vessel area detecting method will be described. For example, the CPU 71 detects blood vessel areas Bv (see FIG. 3), based on luminance values of OCT data (such as a tomographic image) 80. The blood vessel areas Bv are, for example, areas where blood vessels exist. For example, from a single portion (a single layer) of the OCT data 80, the CPU 71 may detect areas having relatively small luminance values, as candidates for blood vessel scan areas As where blood vessel areas Bv exist. For example, the CPU 71 obtains luminance sums Isum in units of ten pixels on a RPE, and obtains the average $\mu$ and standard deviation $\sigma$ of the luminance sums, and detects A-scan if a luminance sum Isum satisfies the following Expression 1.

[Expression 1]

$$I_{sum} < \mu - \sigma \quad (1)$$

For example, from the candidates for blood vessel scan areas As, the CPU 71 detects areas having widths of four or more pixels, as blood vessel scan areas As. This method is based on a result that, in OCT data acquired by an OCT device, luminance values of areas positioned below blood vessels are small due to attenuation in signal intensity. This is because the influence of the blood vessels makes it difficult for the measurement light to reach the areas positioned below the blood vessels, or makes it difficult for reflected light from the areas positioned below the blood vessels to be received.

Figure 3:
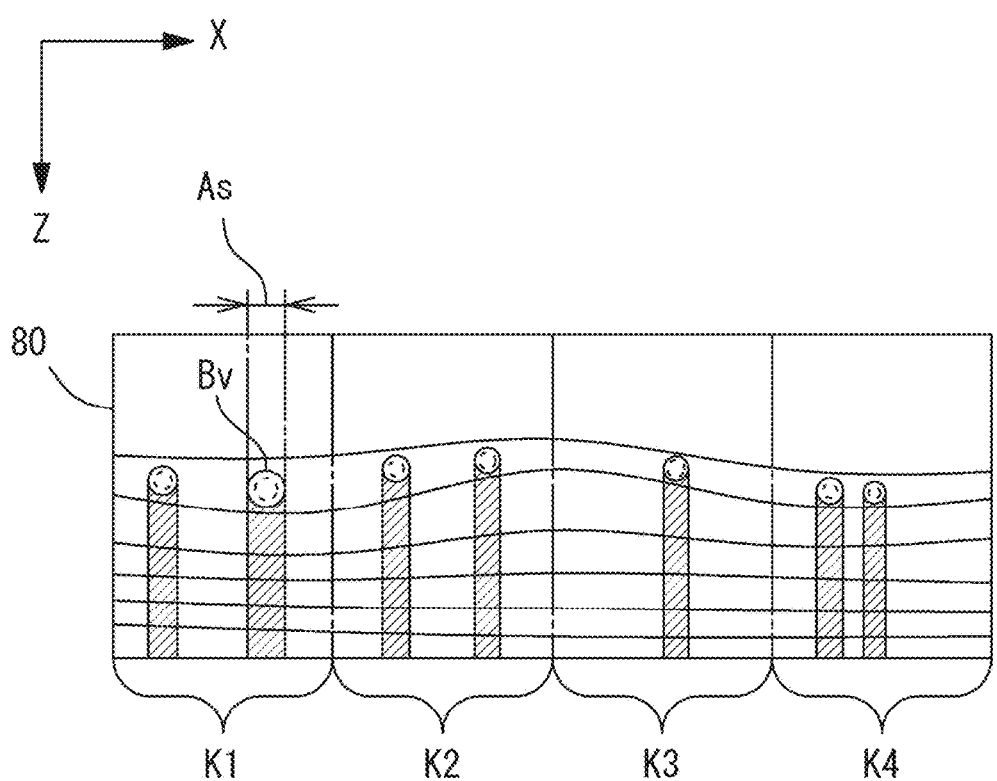
FIG. 3 is a view for explaining a blood vessel area.

The CPU 71 may divide the OCT data 80 into a plurality of sections in the direction of the surface of the fundus, and perform calculation of Expression 1 with respect to each section. For example, the CPU may divide the OCT data 80 into four sections K1 to K4 as shown in FIG. 3, and detects blood vessel scan areas As by Expression 1. In this case, it is possible to suppress the influence of a difference in depth of the fundus on an analysis result.

<Blood Vessel Diameter Detection (Step S2)>

Figure 4A:
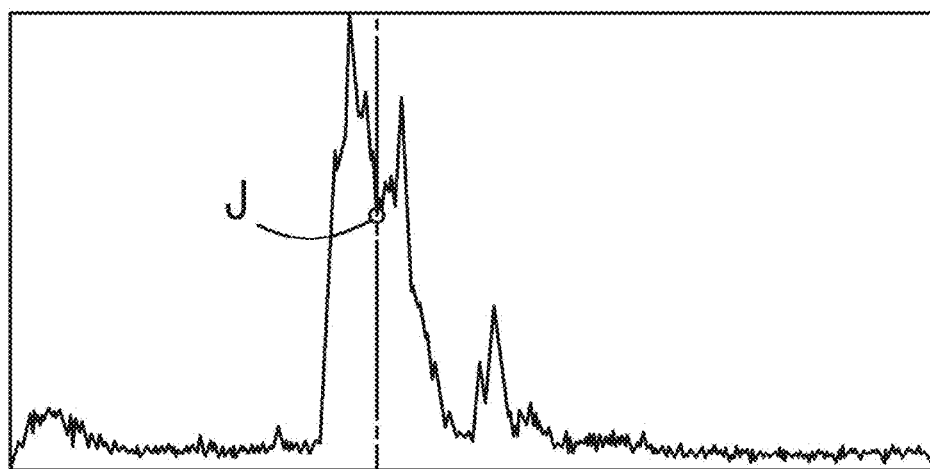
FIG. 4A and FIG. 4B are views illustrating an A-scan profile.

Subsequently, with respect to each blood vessel scan area As detected in STEP S1, the CPU 71 obtains the center, inner diameter, and outer diameter of each blood vessel. In blood vessel areas Bv included in the blood vessel scan areas As, the walls of blood vessels have high luminance, and the centers of the blood vessels have low luminance. Therefore, for example, from a luminance value profile of A-scan of the center of a blood vessel (see FIG. 4A), the CPU 71 detects the lowest point J of a portion convex downward, as the center of the blood vessel. For example, with respect to a range from an inner limiting membrane (ILM) to the boundary between an inner plexiform layer (IPL) and an inner nuclear layer (INL), the CPU 71 obtains the highest luminance Iu of twenty pixels positioned on the upper side from each attention point and the highest luminance Id of twenty pixels positioned on the lower side from the corresponding attention point, and calculates the following Expression 2 with the luminance value Ix of the corresponding attention point, and detects a point having the largest result value as the center of a blood vessel.

[Expression 2]

$$(I_u - I_x) + (I_d - I_x) \quad (2)$$

<Inner Diameter and Outer Diameter>

Figure 4B:
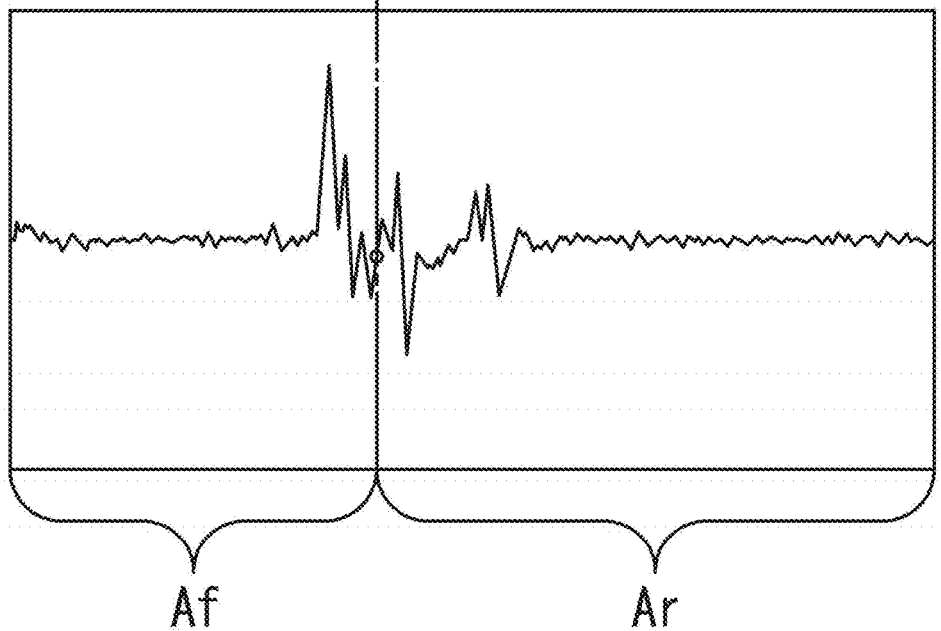
Figure 5:
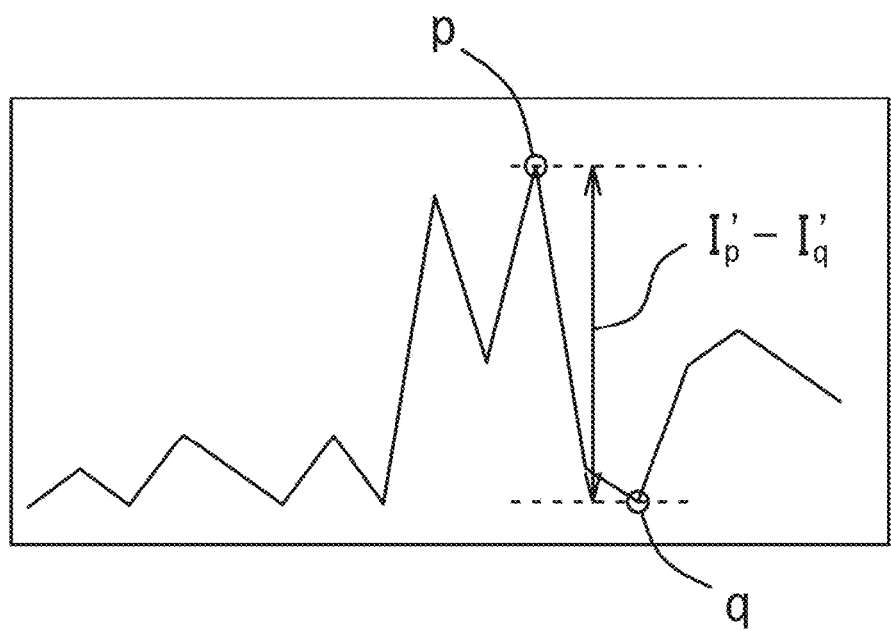
FIG. 5 is a view for explaining blood vessel analysis.

Subsequently, the CPU 71 obtains the inner diameter and outer diameter of each blood vessel by the upper side and lower side from the center of its center. In the vicinity of a bright point of a blood vessel wall, since change in luminance value is drastic, and change in differential value in a vertical direction is great. Therefore, for example, based on change in differential value, the CPU 71 detects a blood vessel wall. For example, the CPU 71 divides a vertical differential profile of A-scan passing through the center of the blood vessel (see FIG. 4B), into an upper area Af and a lower area Ar with reference to the point J representing the center of the blood vessel, and obtains an upward convex point p and a downward convex point q which are consecutive, from each area. Subsequently, the CPU 71 detects points p and q at which a difference (the following Expression 3) between a differential value I'p corresponding to the point p and a differential value I'q corresponding to the point q is largest, as bright points of the blood vessel, and defines the point p and the point q as the outer surface side and inner surface side of the blood vessel wall, respectively (see FIG. 5). The CPU 71 obtains the inner diameter and the outer diameter from the positions of the points p and q of the area Af and the positions of the points p and q of the area Ar.

[Expression 3]

$$I'_p - I'_q \quad (3)$$

<Artery/Vein Determination (Step S3)>

Subsequently, the CPU 71 determines whether each blood vessel detected in STEP S1 is an artery or a vein. For example, the CPU 71 determines whether each blood vessel of the subject eye is an artery or a vein, based on the luminance values of the OCT data. The results of artery/vein determination may be used, for example, to calculate an arteriovenous ratio (hereinafter, also referred to as an AV ratio) to be described below.

Figure 6:
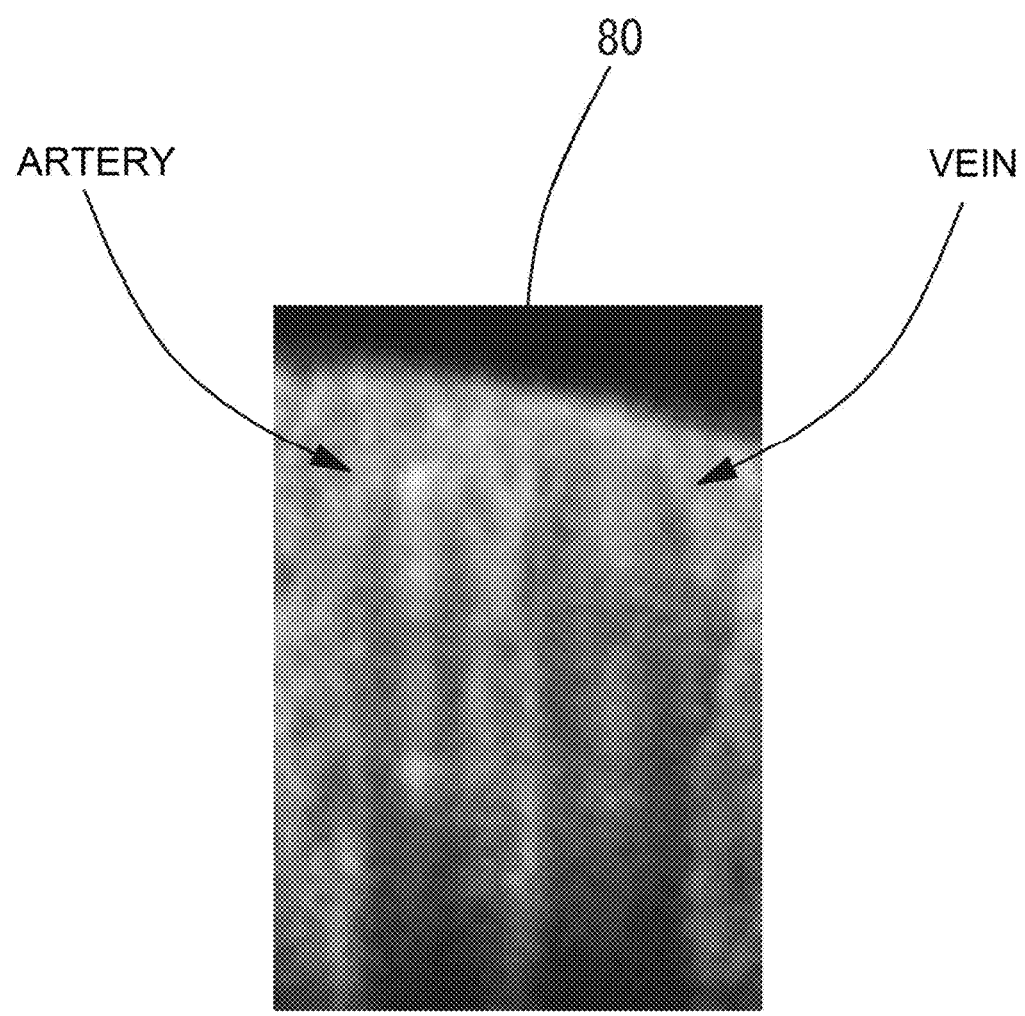
FIG. 6 is a view illustrating OCT data including an artery and a vein.
Figure 7:
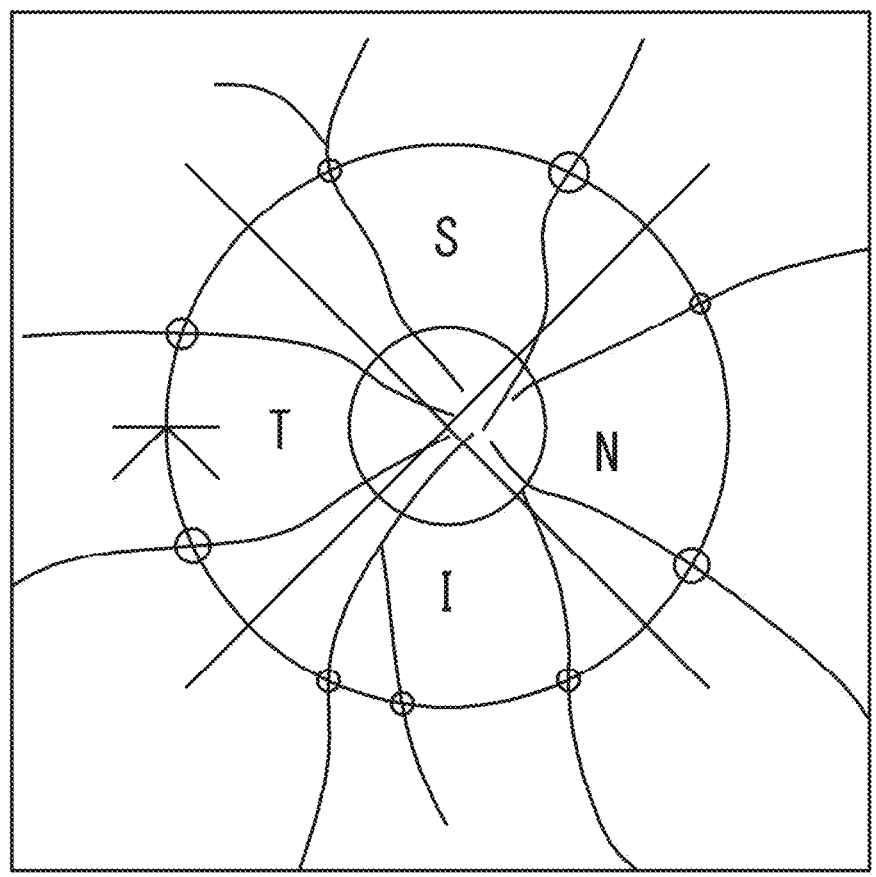
FIG. 7 is a view illustrating a fundus front image.

For example, as shown in FIG. 6, in OCT data, arteries are displayed bright, and veins are displayed so as to be darker than the arteries. Therefore, the CPU 71 performs artery/vein determination based on the luminance values of blood vessels. For example, the CPU 71 performs artery/vein determination using the luminance average of blood vessel scan areas As of each of TSNIT areas of the fundus as shown in FIG. 7. With respect to each of the TSNIT areas, the CPU 71 calculates the luminance average of blood vessel scan areas As in the range from the ILM to the boundary between the IPL and the INL, and determines a threshold at which interclass variance becomes maximum, by a discriminant analysis method. The CPU 71 determines blood vessels having luminance higher than the threshold, as arteries, and determines vessels having luminance lower than the threshold, as veins.

As described above, the OCT data processing device of the present example can perform artery/vein determination based on OCT data of a subject eye. In this case, it is possible to efficiently perform determination of blood vessels unlikely to be checked on a front image acquired by a fundus camera or the like. Further, OCT data can have a resolution higher than that of a front image with respect to a depth direction (a Z direction). Therefore, it is possible to more accurately perform detection on blood vessels of a subject eye. The center positions, inner diameters, outer diameters, and the like of blood vessels acquired based on a tomographic image of the blood vessels are helpful to diagnosis on a subject eye.

For example, as shown in FIG. 6, from the blood vessel walls of arteries on OCT data, high intensities are detected. Therefore, the CPU 71 may perform artery/vein determination based on the luminance values of blood vessel walls. For example, the CPU 71 determines whether the luminance value of each blood vessel wall detected in STEP S2 is equal to or larger than a threshold, or not. For example, if the luminance value of a blood vessel wall is equal to or larger than the threshold, the CPU 71 determines that the corresponding blood vessel is an artery; whereas if the luminance value of a blood vessel wall of the depth direction is smaller than the threshold, the CPU determines that the corresponding blood vessel is a vein.

Figure 8:
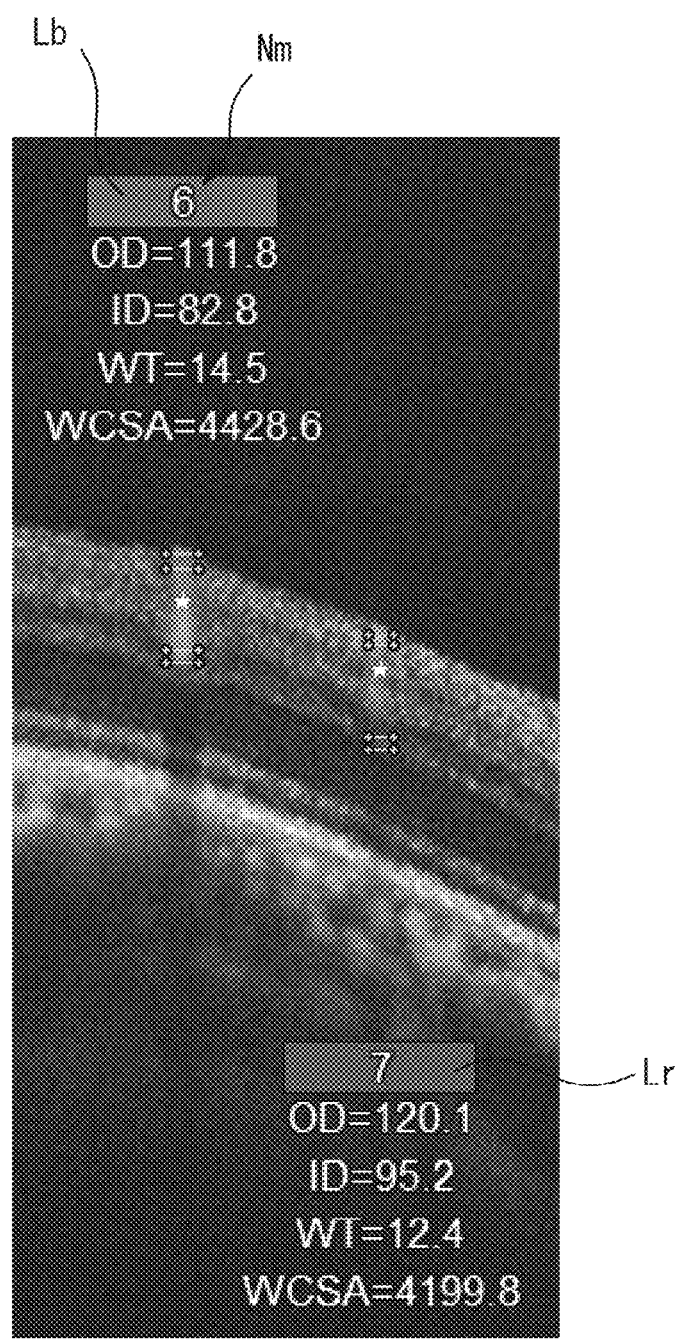
FIG. 8 is a view illustrating OCT data including an artery and a vein.

On OCT data, as shown in FIG. 8, parts of the RPE positioned below veins are darker than parts of the RPE positioned below arteries. Therefore, the CPU 71 may perform artery/vein determination based on the luminance values of the RPE. For example, if a luminance value of the RPE in a blood vessel scan area As is equal to or larger than a threshold, the CPU 71 determines that a corresponding blood vessel is an artery; whereas if a luminance value of the RPE in a blood vessel scan area As is smaller than the threshold, the CPU determines that a corresponding blood vessel is a vein.

<Calculation of OD Value, Id Value, and Wall Thickness>

Subsequently, based on the outer diameter OD and inner diameter ID of each blood vessel, the CPU 71 calculates a wall thickness WT.

[Expression 4]

$$WT = \frac{OD - ID}{2} \quad (4)$$

Further, the CPU 71 calculates the wall cross section area (WCSA) of each blood vessel wall. Each WCSA can be defined, for example, by the following expression.

[Expression 5]

$$WCSA = \frac{\pi}{4}(OD^2 - ID^2) \quad (5)$$

<Display of Blood Vessel Information>

Figure 9:
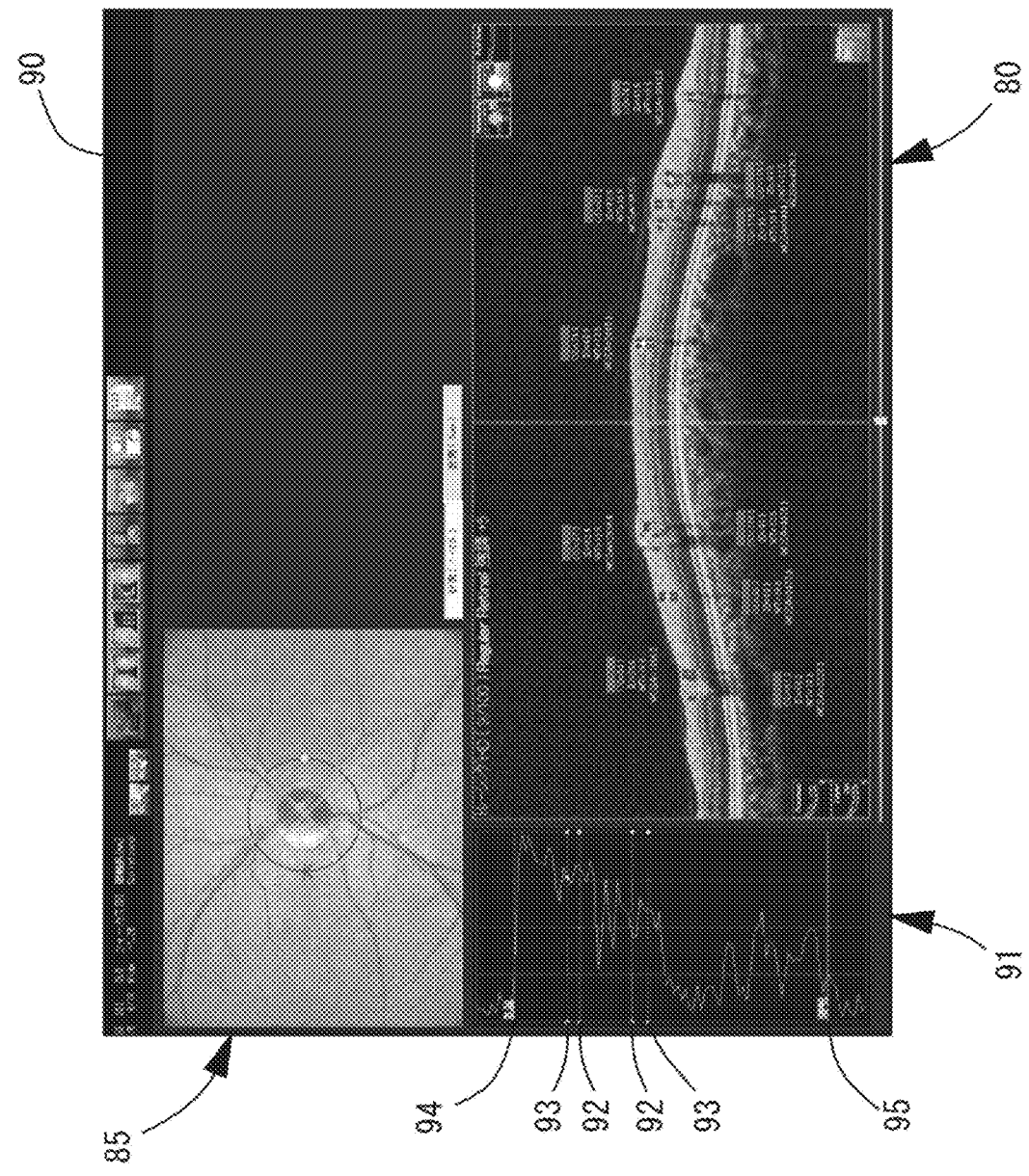
FIG. 9 is a view illustrating an example of a blood vessel analysis screen.

Now, blood vessel information which is displayed on the display unit will be described. The CPU 71 may display a blood vessel information screen 90 on the display unit 75, as shown in FIG. 9. The CPU 71 may display, for example, the results of artery/vein determination, the positions of blood vessels, the results of blood vessel analysis, and so on, on the blood vessel information screen 90. In the present example, the OCT data 80, a fundus front image 85, an A-scan profile 91, and so on displayed the blood vessel information screen 90, blood vessel information is displayed.

Figure 10:
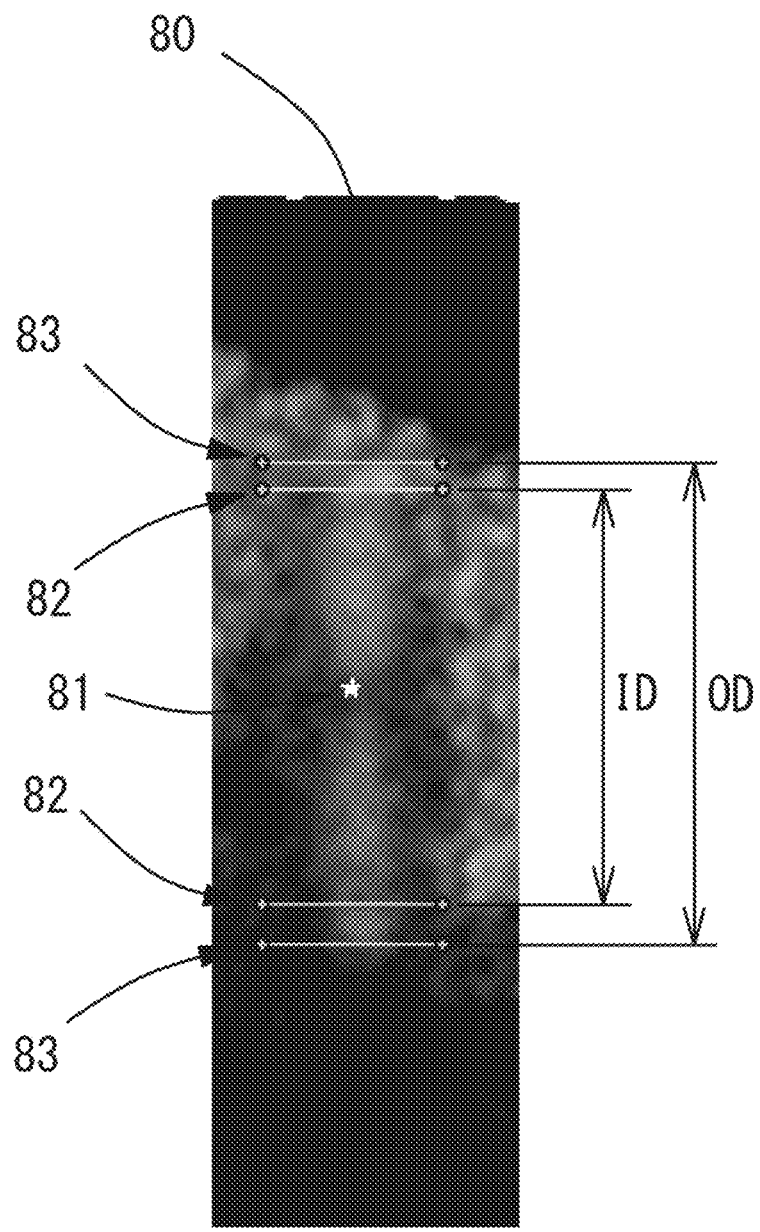
FIG. 10 is a view for explaining the center, inner diameter, and outer diameter of a blood vessel.

For example, the CPU 71 may display the centers, inner diameters, and outer diameters of the blood vessels on the blood vessel information screen 90. For example, as shown in FIG. 10, the CPU 71 may display marks representing the centers, inner diameters, and outer diameters of the blood vessels on the OCT data 80 and the like. For example, FIG. 10 is an enlarged view of a portion of the OCT data 80 displayed on the blood vessel information screen 90. As shown in FIG. 10, the CPU 71 may display center marks 81 representing the centers of the blood vessels, inner-diameter lines 82 representing the inner diameters ID of the blood vessels, and outer-diameter lines 83 representing the inner diameters OD of the blood vessels, on the OCT data 80 displayed on the blood vessel information screen 90. For example, the center marks 81 are displayed at the positions of the centers of the blood vessels detected as described above. For example, an inner-diameter line 82 or outer-diameter line 83 of a blood vessel may be a line extending in a direction (a B-scan direction) crossing a corresponding blood vessel scan area As and representing the position of the inner surface or outer surface of the blood vessel in the depth direction.

As shown in FIG. 9, the A-scan profile 91 may be, for example, a luminance value or luminance gradient profile. Obviously, the CPU 71 may display luminance values and luminance gradients, switchably or at the same time. The CPU 71 may display the A-scan profile 91 of blood vessels on OCT data selected by the operation unit 76, on the blood vessel information screen 90. Similarly on the OCT data 80, even on the A-scan profile 91, inner-diameter lines 92 and outer-diameter lines 93 of blood vessels may be displayed. In this case, the display positions of the inner-diameter lines 82 correspond to the display positions of the inner-diameter lines 92, and the display positions of the outer-diameter lines 83 correspond to the display positions of the outer-diameter lines 93. Therefore, based on the graph of the A-scan profile 91, it is possible to check whether the positions of the inner surface and outer surface of each blood vessel have been appropriately set. The CPU 71 may display the position of a blood vessel layer on the A-scan profile 91. For example, the CPU 71 may display an ILM line 94 representing the position of the ILM, a RPE line 95 representing the position of the RPE, and so on, on the A-scan profile 91, as shown in FIG. 9.

It may be possible for the examiner to edit a result obtained by automatic analysis of the CPU 71. For example, it may be possible for the examiner to edit an analysis result by operating the operation unit 76. For example, the examiner may select a blood vessel to be edited. For example, based on an operation signal output from the operation unit 76, the CPU 71 may transition to a blood vessel edit mode. In the blood vessel edit mode, the examiner may reset the inner diameter ID or outer diameter OD of a blood vessel by the operation unit 76. For example, it may be possible for the examiner to freely move the center marks 81, inner-diameter lines 82, and the outer-diameter lines 83 on the OCT data 80. For example, in a case where the operation unit 76 is a computer mouse, the examiner may move any one of the center marks 81, the inner-diameter lines 82, and the outer-diameter lines 83 on the OCT data 80, by performing a drag operation on the mouse. Similarly, the CPU 71 may move the inner-diameter lines 92 and the outer-diameter lines 93 of the A-scan profile based on operation signals from the operation unit 76.

In a case where the CPU 71 changes the positions of inner surfaces or outer surfaces on the OCT data 80, based on operation signals from the operation unit 76, the CPU 71 may change the positions of corresponding inner-diameter lines 82 or corresponding outer-diameter lines 83 displayed on the A-scan profile. Obviously, in a case where the positions of inner-diameter lines 92 or outer-diameter lines 93 of the A-scan profile 91 are moved, the CPU 71 may change the positions of corresponding inner-diameter lines 82 or corresponding outer-diameter lines 83 on the OCT data 80. In this case, the examiner can correct the positions of inner surfaces or outer surfaces while checking both of the OCT data 80 and the A-scan profile 91. For example, the examiner can sensuously adjust the positions of the marks based on the OCT data 80, and can numerically adjust the positions of the marks on the A-scan profile 91.

<Addition of Blood Vessel Area>

It may be possible for the examiner to additionally register a blood vessel area Bv in a manual manner. For example, the examiner selects the position of the center of a blood vessel on the OCT data 80 by operating the operation unit 76. Thereafter, as described above, the examiner may set the positions of the inner surface and outer surface of the wall of the blood vessel by operating the operation unit 76. The CPU 71 may display marks on the OCT data 80, for example, based on the positions of the center, inner surface, and outer surface of the selected blood vessel.

<Display of Arteriovenous Information>

The CPU 71 may display, for example, the results of artery/vein determination. For example, the CPU 71 may display artery/vein identification labels for individual detected blood vessels on the OCT data 80, as shown in FIG. 9. For example, the CPU may display red labels Lr for arteries, and display blue labels Lb for veins. The CPU 71 may display the number Nm of each blood vessel obtained by performing counting from the ear side, on a corresponding label, as shown in FIG. 9.

<Edit of Arteriovenous Information>

It may be possible for the examiner to manually change an artery/vein label. For example, the examiner selects a corresponding blood vessel area Bv by operating the operation unit 76. In the blood vessel edit mode, it may be possible to designate items such as "ARTERY", "VEIN", and "UNDESIGNATED" on a context menu. The CPU 71 may delete a blood vessel area Bv if a "DELETE" button is pushed.

Also, as shown in FIG. 9, the CPU 71 may display the positions of the blood vessels determined by the information based on the OCT data 80, and artery/vein identification labels, on the fundus front image 85 acquired by the front observation optical system 200. In this case, it is easy to check the positional relationship between the arteries and veins of the fundus front image 85.

The CPU 71 may display the OCT data 80 and the A-scan profile 91 such that they overlap. In this case, the examiner can edit the positions of the centers, inner surfaces, outer surfaces of the blood vessel areas By, and so on while checking both of the OCT data 80 and the profile 91. It is easy for the examiner to check the correspondence between the OCT data 80 and the A-scan profile 91.

The CPU 71 may display a portion the OCT data 80 corresponding to detected blood vessels in a larger size. In this case, it is easy for the examiner to observe the appearances of the blood vessels on the OCT data 80.

The CPU 71 may calculate an AV ratio. An AV ratio is, for example, an arteriovenous ratio. For example, the CPU 71 may obtain the thickness of the blood vessel wall of each of an artery and a vein, and obtain a thickness ratio between the blood vessel walls of the artery and the vein. In this case, the CPU 71 can present information helpful to blood vessel state diagnosis. The CPU 71 may obtain a size ratio between an artery and a vein.

The CPU 71 may calculate the degree of circularity of the subject eye E from the blood vessel information acquired based on the OCT data 80. For example, the CPU may calculate a ratio between the transverse width and longitudinal width of a blood vessel area By. In this case, the CPU 71 can present information for diagnosing whether the shape of a blood vessel is normal or not.

The CPU 71 may hold blood vessel analysis information, and display the blood vessel analysis information and image data of the same patient acquired on different days, side by side. In this case, it is easy for the examiner to compare information on an examinee, such as the depths, sizes, and wall thicknesses on blood vessels, with values of the past.

Also, the CPU 71 may acquire a motion contrast image of a subject eye. A motion contrast image can be acquired, for example, based on an OCT signal acquired by scanning the same position on a fundus data with the OCT optical system 100, a plurality of times. Motion contrast is, for example, information representing motion of an object. For example, motion contrast of a subject eye is information representing a blood flow in the fundus of the subject eye. Therefore, the OCT data processing device 1 may use information on the results of artery/vein determination based on the OCT data 80, for example, in a motion contrast image of the subject eye. For example, the OCT data processing device may control the display unit 75 such that the display unit displays a label or the like for identifying whether the route of each blood vessel included in a motion contrast image.

The CPU 71 may extract either arteries or veins with respect to blood vessels of OCT data, thereby substantially performing artery/vein determination on blood vessels.

Figure 2:
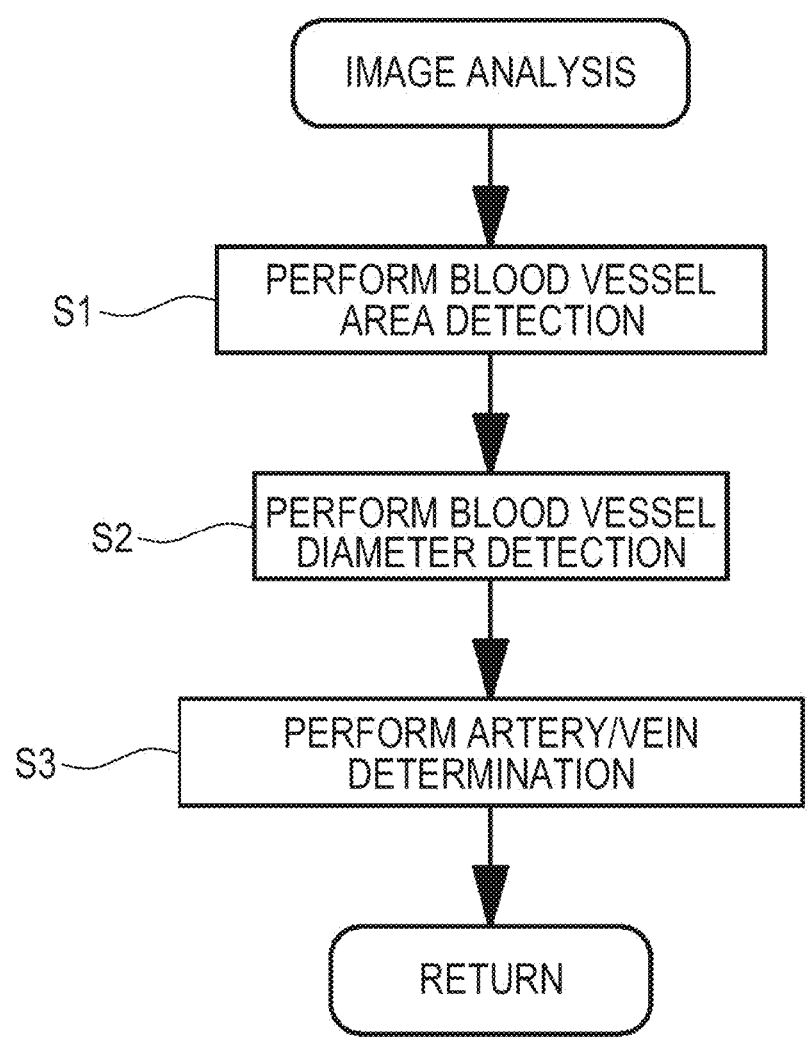
FIG. 2 is a flow chart illustrating a control operation of the example.

In the following examples, as shown in the flow chart of FIG. 2, the CPU calculates the diameters of blood vessels, thereby performing artery/vein determination. However, the CPU may perform artery/vein determination without calculating the diameters of blood vessels.

What is claimed is:

1. An optical coherence tomography (OCT) data processing device for processing OCT data of a subject eye, comprising:
   a processor; and
   memory storing computer readable program, when executed by the processor, causing the OCT data processing device to execute:
   acquiring OCT data from an OCT optical system; and
   analyzing the acquired OCT data to acquire arteriovenous information on the blood vessel based on image information on a blood vessel scan area including a blood vessel of the subject eye;
   wherein the computer readable program when executed by the processor causes the OCT data processing device to detect a blood vessel wall from the blood vessel scan area, and acquire the arteriovenous information on the blood vessel based on luminance information on the blood vessel wall;
   wherein with respect to the blood vessel scan area, the computer readable program when executed by the processor causes the OCT data processing device to compare luminance values of the blood vessel wall and a hollow surrounded by the blood vessel wall,
   the computer readable program when executed by the processor causes the OCT data processing device to acquire the arteriovenous information representing that the blood vessel is an artery in a case that the luminance value of the blood vessel wall is larger than the luminance value of the hollow, and
   the computer readable program when executed by the processor causes the OCT data processing device to acquire the arteriovenous information representing that the blood vessel is a vein in a case that the luminance value of the blood vessel wall is smaller than the luminance value of the hollow.

2. An optical coherence tomography (OCT) data processing device for processing OCT data of a subject eye, comprising:
   a processor; and
   memory storing computer readable program, when executed by the processor, causing the OCT data processing device to execute:
   acquiring OCT data from an OCT optical system; and
   analyzing the acquired OCT data to acquire arteriovenous information on the blood vessel based on image information on a blood vessel scan area including a blood vessel of the subject eye;
   wherein the computer readable program when executed by the processor causes the OCT data processing device to specify a plurality of the blood vessel scan areas corresponding respectively to a plurality of the blood vessels, based on the OCT data, and compare the image information of the OCT data corresponding to the plurality of specified blood vessel scan area to acquire the arteriovenous information on the plurality of blood vessels; and
   wherein the computer readable program when executed by the processor causes the OCT data processing device to compare luminance values of the plurality of blood vessel scan areas,
   with respect to the blood vessel scan area which is included in the plurality of blood vessel scan areas and has a relatively large luminance value, the computer readable program when executed by the processor causes the OCT data processing device to acquire the arteriovenous information representing that the blood vessel is an artery, and
   with respect to a blood vessel scan area which is included in the plurality of blood vessel scan areas and has a relatively small luminance value, the computer readable program when executed by the processor causes the OCT data processing device to acquire the arteriovenous information representing that the blood vessel is a vein.

3. An optical coherence tomography (OCT) data processing device for processing OCT data of a subject eye, comprising:
   a processor; and
   memory storing computer readable program, when executed by the processor, causing the OCT data processing device to execute:
   acquiring OCT data from an OCT optical system; and
   analyzing the acquired OCT data to acquire arteriovenous information on the blood vessel based on image information on a blood vessel scan area including a blood vessel of the subject eye;
   wherein the computer readable program when executed by the processor causes the OCT data processing device to separate a fundus included in the OCT data into a plurality of layers, and compare image information on parts of at least one of the plurality of separate layers corresponding to the plurality of blood vessel scan areas to acquire the arteriovenous information on the plurality of blood vessels; and
   wherein the computer readable program when executed by the processor causes the OCT data processing device to compare luminance values of at least one layer of the plurality of layers for one of the plurality of blood vessel scan areas with the luminance values of said at least one layer for another of the plurality of blood vessel scan areas, with respect to the blood vessel scan area which is included in the plurality of blood vessel scan areas and has a relatively large luminance value, the computer readable program when executed by the processor causes the OCT data processing device to acquire the arteriovenous information representing that the blood vessel is an artery, and with respect to the blood vessel scan area which is included in the plurality of blood vessel scan areas and has a relatively small luminance value, the computer readable program when executed by the processor causes the OCT data processing device to acquire the arteriovenous information representing that the blood vessel is a vein.

4. The OCT data processing device according to claim 1, wherein:

the computer readable program when executed by the processor causes the OCT data processing device to change the arteriovenous information based on an operation signal output in response to an operation on an operation unit.

5. The OCT data processing device according to claim 1, further comprising:

the computer readable program when executed by the processor causes the OCT data processing device to control display of a display, in such a manner that the display displays the arteriovenous information.

6. The OCT data processing device according to claim 5, wherein:

the computer readable program when executed by the processor causes the OCT data processing device to control the display in such a manner that the display displays the arteriovenous information on a front image of a fundus of the subject eye.

7. The OCT data processing device according to claim 5, wherein:

the computer readable program when executed by the processor causes the OCT data processing device to control the display in such a manner that the display displays the arteriovenous information on a three-dimensional motion contrast image acquired by the OCT optical system.

8. The OCT data processing device according to claim 5, wherein:

the computer readable program when executed by the processor causes the OCT data processing device to control the display to display an A-scan profile corresponding to the blood vessel scan area, together with the OCT data.

9. The OCT data processing device according to claim 8, wherein:

the computer readable program when executed by the processor causes the OCT data processing device to control the display to display a first mark representing the position of the center or blood vessel wall of the blood vessel of the blood vessel scan area in an A-scan direction, on the OCT data.

10. The OCT data processing device according to claim 8, wherein:

the computer readable program when executed by the processor causes the OCT data processing device to control the display to display a second mark representing the position of the center or blood vessel wall of the blood vessel of the blood vessel scan area in an A-scan direction, on the A-scan profile.

11. The OCT data processing device according to claim 9, wherein:

the computer readable program when executed by the processor causes the OCT data processing device to control the display to change the first mark or the second mark based on an operation signal output in response to an operation on an operation unit.

12. The OCT data processing device according to claim 11, wherein:

while changing the position of one of the first mark and the second mark, the computer readable program when executed by the processor causes the OCT data processing device to control the display to change the position of the other of the first mark and the second mark.

13. The OCT data processing device according to claim 10, wherein:

the first mark or the second mark represents at least one of the position of the outer surface of the blood vessel in the A-scan direction, the position of the inner surface of the blood vessel in the A-scan direction, and the position of the center of the blood vessel in the A-scan direction.

14. The OCT data processing device according to claim 8, wherein:

the computer readable program when executed by the processor causes the OCT data processing device to control the display to display the OCT data and the A-scan profile while the A-scan profile is overlapped with the OCT data.

15. The OCT data processing device according to claim 8, wherein:

the computer readable program when executed by the processor causes the OCT data processing device to switch the A-scan profile between a luminance profile and a gradient profile.

16. A non-transitory computer readable medium storing an optical coherence tomography (OCT) data processing program which is executable in an OCT data processing device configured to process OCT data of a subject eye, and is executed by a processor of the OCT data processing device, the OCT data processing program when executed by the OCT data processing device causing the OCT data processing device to execute:

acquiring OCT data from an OCT optical system; and analyzing the OCT data to acquire arteriovenous information on a blood vessel of the subject eye based on image information on a blood vessel scan area including the blood vessel;

wherein the OCT data processing program when executed by the by the OCT data processing device causes the OCT data processing device to detect a blood vessel wall from the blood vessel scan area, and acquire the arteriovenous information on the blood vessel based on luminance information on the blood vessel wall;

wherein with respect to the blood vessel scan area, the OCT data processing program when executed by the OCT data processing device causes the OCT data processing device to compare luminance values of the blood vessel wall and a hollows surrounded by the blood vessel wall, the OCT data processing program when executed by the OCT data processing device causes the OCT data processing device to acquire the arteriovenous information representing that the blood vessel is an artery in a case that the luminance value of the blood vessel wall is larger than the luminance value of the hollow, and the OCT data processing program when executed by the OCT data processing device causes the OCT data processing device to acquire the arteriovenous information representing that the blood vessel is a vein in a case that the luminance value of the blood vessel wall is smaller than the luminance value of the hollow.

* * * * *